United States Patent
Vértesy et al.

[11] Patent Number: 5,891,851
[45] Date of Patent: Apr. 6, 1999

[54] ANTIBIOTIC, FEGLYMYCIN, PROCESSES FOR ITS PREPARATION AND ITS USE

[75] Inventors: Laszló Vértesy, Eppstein; Martin Knauf, Frankfurt; Joachim Wink, Rödermark; Dieter Isert, Eschborn; Wilhelm Stahl, Idstein; Günther Riess, Hattersheim, all of Germany; Jozsef Aszodi, Pontault Combault; Dominique Le Beller, Jaux, both of France

[73] Assignee: Hoechst Aktiengesellschaft, Frankfurt am Main, Germany

[21] Appl. No.: 988,552

[22] Filed: Dec. 11, 1997

[30] Foreign Application Priority Data

Dec. 13, 1996 [DE] Germany ............ 196 52 008.8

[51] Int. Cl.$^6$ .............. A61K 38/00; A61K 38/02; C07K 5/00; C07K 7/00
[52] U.S. Cl. .............. 514/14; 530/327; 514/2; 514/21
[58] Field of Search .............. 514/2, 14, 21; 530/327

[56] References Cited

FOREIGN PATENT DOCUMENTS

| | | |
|---|---|---|
| 0 603 030 | 6/1994 | European Pat. Off. . |
| 0 603 031 | 6/1994 | European Pat. Off. . |
| 0603030 | 6/1994 | European Pat. Off. . |
| 0603031 | 6/1994 | European Pat. Off. . |

OTHER PUBLICATIONS

Olivier Potterat et al., "Aborycin—a Tricyclic 21–Peptide Antibiotic Isolated from *Streptomyces griseoflavus*", Liebigs Ann. Chem. 1994, pp. 741–743.

Maki Nishio et al., "Siamycins I and II, New Anti–HIV Peptides" Journal of Antibiotics, 1995, vol. 48, No. 5, May 1995, pp. 433–434.

Ravin, Louis, "Preformulation," Remington's Pharmaceutical Sciences, 17th Ed., Chapter 76, pp. 1409–1423, (1985).

*Primary Examiner*—Avis M. Davenport
*Attorney, Agent, or Firm*—Finnegan, Henderson, Farabow, Garrett & Dunner, L.L.P.

[57] ABSTRACT

This invention relates to the antibiotic feglymycin, as well as processes for its preparation and use. Feglymycin is represented by the structural formula (SEQ ID NO:1):

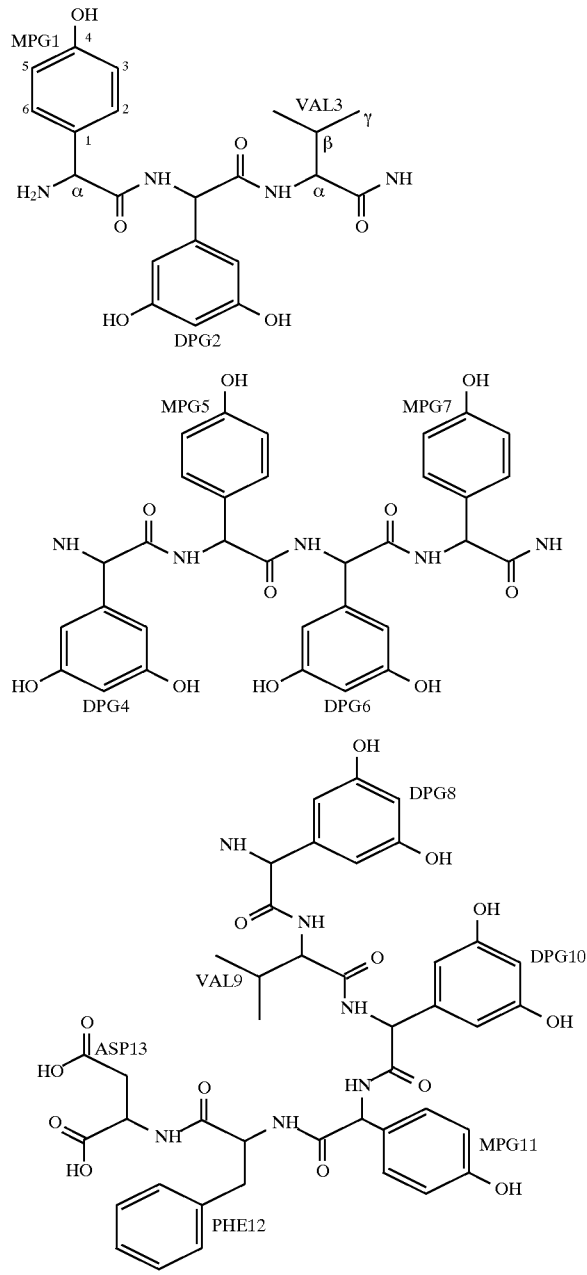

15 Claims, 1 Drawing Sheet

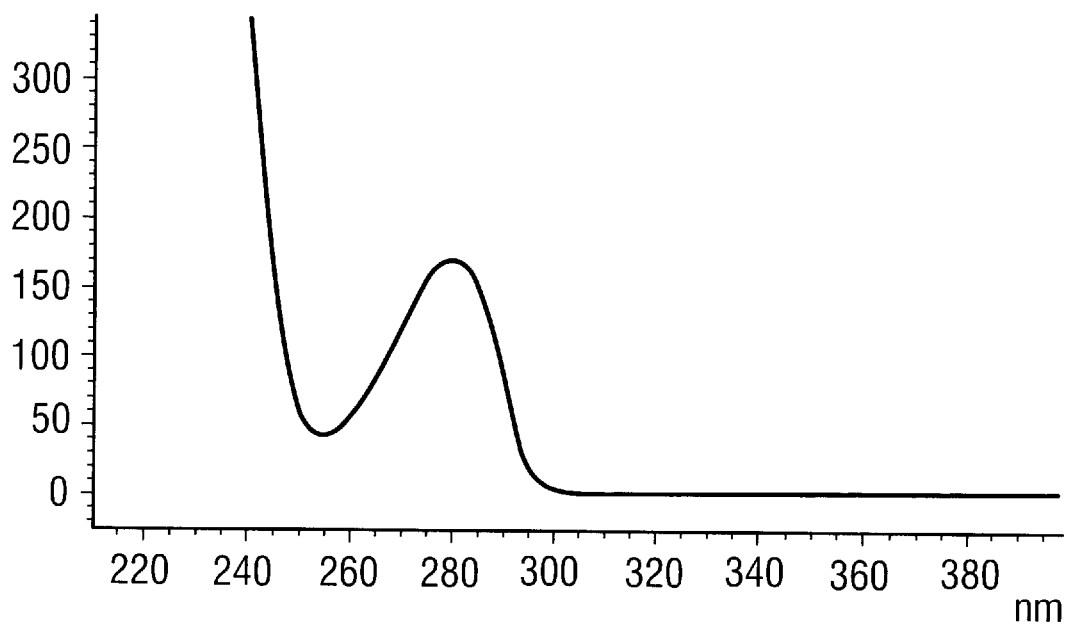

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product= "MPG"

( i x ) FEATURE:
        ( A ) NAME/KEY: Modified-site
        ( B ) LOCATION: 2
        ( D ) OTHER INFORMATION: /product= "DPG"

( i x ) FEATURE:
        ( A ) NAME/KEY: Modified-site
        ( B ) LOCATION: 4
        ( D ) OTHER INFORMATION: /product= "DPG"

( i x ) FEATURE:
        ( A ) NAME/KEY: Modified-site
        ( B ) LOCATION: 5
        ( D ) OTHER INFORMATION: /product=0 "MPG"

( i x ) FEATURE:
        ( A ) NAME/KEY: Modified-site
        ( B ) LOCATION: 6
        ( D ) OTHER INFORMATION: /product= "DPG"

( i x ) FEATURE:
        ( A ) NAME/KEY: Modified-site
        ( B ) LOCATION: 7
        ( D ) OTHER INFORMATION: /product= "MPG"

( i x ) FEATURE:
        ( A ) NAME/KEY: Modified-site
        ( B ) LOCATION: 8
        ( D ) OTHER INFORMATION: /product= "DPG"

( i x ) FEATURE:
        ( A ) NAME/KEY: Modified-site
        ( B ) LOCATION: 10
        ( D ) OTHER INFORMATION: /product= "DPG"

( i x ) FEATURE:
        ( A ) NAME/KEY: Modified-site (B) LOCATION: 11
(D) OTHER INFORMATION: /product= "MPG"

(xi) SEQUENCE DESCRIPTION: SEQ ID NO:1:

```
Xaa Xaa Val Xaa Xaa Xaa Xaa Xaa Val Xaa Xaa Phe Asp
1               5                       10
```

ANTIBIOTIC, FEGLYMYCIN, PROCESSES FOR ITS PREPARATION AND ITS USE

BACKGROUND OF THE INVENTION

The present invention relates to the novel antibiotic feglymycin, processes for its preparation and its use.

A large number of antibiotics have been employed therapeutically for the treatment of bacterial infectious diseases. The pathogens, however, are becoming increasingly resistant to the pharmaceuticals used, and there is even the threat of great danger due to so-called multiresistant bacteria, which have become resistant not only to individual groups of antibiotics, such as, for example, β-lactam antibiotics or glycopeptides or macrolides, but simultaneously carry several resistances. There are even pathogens which have become resistant to all commercially available antibiotics, and infectious diseases which are caused by such bacteria can no longer be treated. There is therefore a great need for new agents which can be employed against resistant bacteria. Indeed, many thousands of antibiotics have been described in the literature, which, however, are mostly too toxic to be able to be employed as pharmaceuticals.

The development of resistance also presents a problem in the control of immunodeficiency, the so-called AIDS condition, which is caused by the new type of virus, the "human immunodeficiency virus" (HIV). There is still no medicament for curing an AIDS condition. The agents which have been employed until now can admittedly prolong the life expectancy of HIV-infected persons, but due to the formation of resistant viruses, medicine urgently needs novel, nontoxic virostatics.

SUMMARY OF THE INVENTION

It has surprisingly been found that the Streptomyces spec. HAG 4675, DSM 11 171 is able to form a novel antibiotic, feglymycin, which is not only antibacterially active and highly tolerable, but also effectively inhibits [the] "human immunodeficiency" viruses.

The invention accordingly relates to the compound feglymycin, to its physiologically tolerable salts and to its obvious chemical equivalents. Feglymycin has an empirical formula of $C_{95}H_{97}N_{13}O_{30}$, MW 1900.90, and is represented by the structural formula (SEQ ID NO:1):

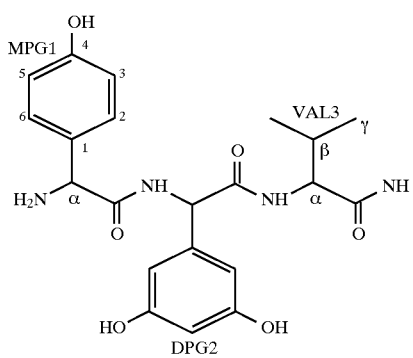

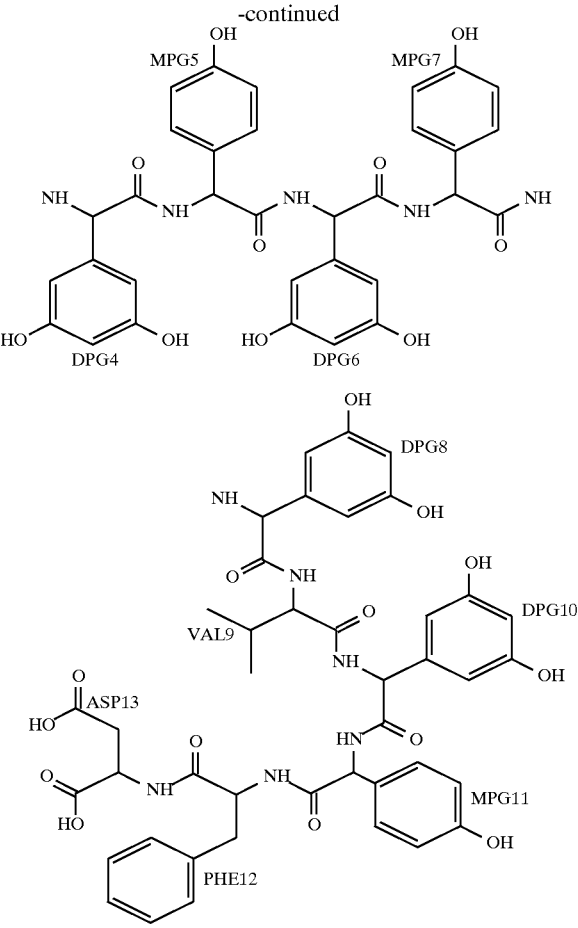

Owing to the empirical and structural formulae indicated, the antibiotic feglymycin differs from substances known in the literature. The compound according to the invention has a characteristic ultraviolet spectrum.

The subject matter of the present invention furthermore includes processes for the preparation of the compounds mentioned. One process for the preparation of the compounds mentioned comprises culturing the microorganism Streptomyces species HAG 4674 (DSM 11171) in an aqueous nutrient medium and then isolating and purifying the target compounds. This microorganism was deposited on Sep. 24, 1996 under the conditions of the Budapest Convention in the German Collection of Microorganisms and Cell Cultures, Mascheroder Weg 1b, D-38124 Brunswick under the number DSM 11171.

BRIEF DESCRIPTION OF THE DRAWING

FIG. 1 is an ultaviolet absorption spectrum of feglymycin recorded in methanol.

DETAILED DESCRIPTION OF THE INVENTION

Streptomyces spec. DSM 11171 has a white aerial mycelium and yellow spore chains. It forms the spore chains characteristic of Streptomycetes in spirals. The cell wall contains L,L-diaminopimelic acid as a characteristic amino acid and glucose and also mannose as sugars; these are characteristic features of the genus Streptomyces. In a nutrient solution which contains a carbon source and a nitrogen source as well as the customary inorganic salts, the Streptomyces spec. DSM 11171 produces the compound feglymycin.

Instead of the strain DSM 11171, its mutants and variants can also be employed insofar as they synthesize the compounds according to the invention. Such mutants can be produced in a known manner by physical means, for example irradiation, such as with ultraviolet rays or X-rays, or chemical mutagens, such as, for example, ethyl methanesulfonate (EMS); 2-hydroxy-4-methoxybenzophenone (MOB) or N-methyl-N'-nitro-N-nitrosoguanidine (MNNG).

The screening for mutants and variants which produce the antibiotic according to the invention can be carried out by determination of the biological activity of the active compound accumulated in the culture broth, for example by testing the antibacterial action.

Suitable preferred carbon sources for aerobic fermentation are assimilable hydrocarbons and sugar alcohols, such as glucose, lactose or D-mannitol, and carbohydrate-containing natural products, such as, for example, malt extract. Suitable nitrogen-containing nutrients are: amino acids, peptides and proteins as well as their degradation products, such as peptones or tryptones, furthermore meat extracts, ground seeds, for example of corn, wheat, beans, oats, soybeans or of the cotton plant, distillation residues from alcohol production, meat meals or yeast extracts, and also ammonium salts and nitrates. Inorganic salts which the nutrient solution can contain are, for example, chlorides, carbonates, sulfates or phosphates of the alkali metals or alkaline earth metals, iron, zinc, cobalt and manganese.

The formation of feglymycin proceeds particularly well, for example, in a nutrient solution which contains approximately 0.5 to 5% oat flakes, preferably 1 to 2%, and a trace element solution in a concentration of 0.1 to 0.5%, preferably 0.2 to 0.3%. The trace element solution contains $CaCl_2$, Fe(III) citrate, $MnSO_4$, $ZnCl_2$, $CuSO_4$, sodium tetraborate, $CoCl_2$ and sodium molybdate.

Culturing is carried out aerobically, for example, by submersion with shaking or stirring in shaker flasks or fermenters, and, if appropriate, with introduction of air or oxygen. The fermentation can be carried out, for example, in wide-necked bottles or round-bottomed flasks of various volumes, in glass fermenters or $V_2A$ steel tanks. It can be carried out in a temperature range from approximately 20° to 35° C., preferably at approximately 25° to 30° C. The pH should be between 4 and 10, advantageously between 5.5 and 8.5. The microorganism is cultured under these conditions, in general, over a period of 20 to 300 hours, preferably 24 to 140 hours. Culturing is advantageously carried out in several stages, i.e. one or more precultures are first prepared in a liquid nutrient medium, which are then inoculated into the actual production medium, the main culture, for example in the volume ratio 1:10. The preculture is obtained, for example, by inoculating a sporulated mycelium into a nutrient solution and allowing it to grow for approximately 20 to 120 hours, preferably 24 to 72 hours. The sporulated mycelium can be obtained, for example, by allowing the strain to grow, for example, for 1 to 40 days, preferably 3 to 10 days, on a solid or liquid nutrient medium, for example yeast-malt agar or potato-dextrose agar.

The fermentation course and the formation of the antibiotic feglymycin can be monitored according to methods known to the person skilled in the art, such as, for example, by testing the biological activity in bioassays or by chromatographic methods such as thin-layer chromatography (TLC) or high-performance liquid chromatography (HPLC).

The antibiotic feglymycin can occur both in the mycelium and in the culture filtrate, but usually the main amount is located in the cell matter (mycelium). It is therefore expedient to separate the mycelium from the filtrate by filtration or centrifugation. The filtrate is extracted using an adsorption resin as a solid phase. The mycelium is expediently extracted with methanol or acetone; however, other solvents can also be used.

The extractions can be carried out in a wide pH range; however, it is expedient to work in a neutral or slightly acidic medium, preferably between pH 3 and pH 7. The extracts can be concentrated and dried, e.g. in vacuo.

One method of isolation of the feglymycin is solution partitioning in a manner known per se.

Another method of purification is chromatography on adsorption resins such as, for example, [on] Diaion® HP-20 (Mitsubishi Casei Corp., Tokyo), [on] Amberlite® XAD 7 (Rohm and Haas, USA), [on] Amberchrom® CG (Toso Haas, Philadelphia, USA) or [on] the like. Numerous reverse phase supports, e.g. $RP_{18}$, are moreover suitable, as have been generally made known, for example, in the context of high-pressure liquid chromatography (HPLC).

A further possibility of purification of the antibiotics according to the invention consists in the use of so-called normal phase chromatography supports, such as, for example, silica gel or $Al_2O_3$ or others in a manner known per se.

An alternative isolation method is the use of molecular sieves, such as, for example, Fractogel® TSK HW-40, Sephadex® G-25 and others, in a manner known per se. It is moreover also possible to obtain feglymycin from enriched material by crystallization. Organic solvents and their mixtures, for example, anhydrous or with addition of water, are suitable for this purpose. An additional method for the isolation and purification of the antibiotics according to the invention consists in the use of anion exchangers, preferably in the pH range from 4 to 10 and cation exchangers, preferably in the pH range from 2 to 5. The use of buffer solutions to which portions of organic solvents have been added is particularly suitable for this purpose.

The antibiotic feglymycin or derived chemical derivatives can be converted into the corresponding pharmacologically tolerable salts by methods known to the person skilled in the art.

Obvious chemical equivalents of the compounds according to the invention are compounds which exhibit a slight chemical difference, i.e. have the same activity or are converted into the compounds according to the invention under mild conditions. The equivalents mentioned include, for example, esters, amino derivatives, complexes or adducts of the or with the compounds according to the invention.

Pharmacologically tolerable salts of the compounds according to the invention are understood as meaning both inorganic and organic salts, such as are described in Remington's Pharmaceutical Sciences (17th Edition, page 1418 (1985)). Possible salts are, in particular, alkali metal, ammonium or alkaline earth metal salts, salts with physiologically tolerable amines and salts with inorganic or organic acids such as, for example, HCl, HBr, $H_2SO_4$, maleic acid or fumaric acid.

The physicochemical and spectroscopic properties of the antibiotics according to the invention can be summarized as follows:

Feglymycin:

Appearance: Colorless substance soluble in methanol, acetonitrile and water. Stable in neutral and mildly alkaline medium, but unstable in strongly acidic or strongly alkaline solutions.

Empricial formula: $C_{95}H_{97}N_{13}O_{30}$
Molecular weight: 1900.90
$^1$H-NMR: see Table 1
E max (log ε): 280 nm (4.16)

$$[\alpha]\frac{20}{D} = -106°$$

TABLE 1

$^1$H and $^{13}$C chemical shifts of feglymycin

| Sequence No. | Atom position | $^1$H chem. shift | $^{13}$C chem. shift |
|---|---|---|---|
| MPG1 | NH$_2$ | n.d. | — |
| | αH | 4.982(b) | 54.559(2) |
| | 1 | — | 123.917 |
| | 2,6 | 7.341(m) | 129.170(12) |
| | 3,5 | 6.807(d) | 115.257(4) |
| | 4 | — | 157.870 |
| | OH | 9.730 | — |
| | CO | — | 166.568 |
| DPG2 | NH | 8.928 | — |
| | αH | 5.492 | 56.157 |
| | 1 | — | 140.440 |
| | 2,6 | 6.365 | 105.445 |
| | 3,5 | — | 157.741 |
| | 4 | 6.130 | 101.589 |
| | OH | 9.220 | — |
| | CO | — | 168.603 |
| VAL3 | NH | 7.960 | — |
| | αH | 4.360 | 56.789 |
| | βH | 1.875 | 31.240 |
| | γH | 0.546 | 18.860 |
| | γH | 0.524 | 16.951 |
| | CO | — | 169.798 |
| DPG4 | NH | 8.515 | — |
| | αH | 5.532 | 55.515 |
| | 1 | — | 140.647 |
| | 2,6 | 6.253 | 105.197 |
| | 3,5 | — | 157.573 |
| | 4 | 6.067 | 101.325 |
| | OH | 9.140 | — |
| | CO | — | 168.591 |
| MPG5 | NH | 8.651 | — |
| | αH | 5.611 | 54.680 |
| | 1 | — | 128.298 |
| | 2,6 | 7.065 | 127.775 |
| | 3,5 | 6.554 | 114.530 |
| | 4 | — | 156.180 |
| | OH | 9.281 | — |
| | CO | — | 169.197 |
| DPG6 | NH | 8.774 | — |
| | αH | 5.502 | 55.519 |
| | 1 | — | 140.232 |
| | 2,6 | 6.169 | 105.146 |
| | 3,5 | — | 157.598 |
| | 4 | 6.049 | 101.325 |
| | OH | 9.086 | — |
| | CO | — | 168.591 |
| MPG7 | NH | 8.676 | — |
| | αH | 5.590 | 54.779 |
| | 1 | — | 128.298 |
| | 2,6 | 7.051 | 127.775 |
| | 3,5 | 6.576 | 114.530 |
| | 4 | — | 156.180 |
| | OH | 9.302 | — |
| | CO | — | 169.113 |
| DPG8 | NH | 8.631 | — |
| | αH | 5.400 | 55.893 |
| | 1 | — | 140.666 |
| | 2,6 | 6.200 | 105.086 |
| | 3,5 | — | 157.590 |
| | 4 | 6.047 | 101.325 |
| | OH | 9.085 | — |
| | CO | — | 168.983 |
| VAL9 | NH | 8.126 | — |
| | αH | 4.364 | 56.552 |
| | βH | 1.881 | 31.240 |
| | γH | 0.609 | 17.387 |
| | γH | 0.588 | 18.886 |
| DPG10 | NH | 8.478 | — |
| | αH | 5.458 | 55.503 |
| | 1 | — | 140.559 |
| | 2,6 | 6.290 | 105.428 |
| | 3,5 | — | 157.695 |
| | 4 | 6.084 | 101.393 |
| | OH | 9.154 | — |
| | CO | — | 168.600 |
| MPG11 | NH | 8.519 | — |
| | αH | 5.300 | 55.231 |
| | 1 | — | 128.050 |
| | 2,6 | 6.933 | 127.971 |
| | 3,5 | 6.567 | 114.530 |
| | 4 | — | 156.180 |
| | OH | 9.320 | — |
| | CO | — | 169.216 |
| PHE12 | NH | 8.362 | — |
| | αH | 4.523 | 53.541 |
| | βH | 3.038/2.811 | 37.270 |
| | 1 | — | 137.191 |
| | 2,6 | 7.238 | 129.097 |
| | 3,5 | 7.222 | 127.824 |
| | 4 | 7.160 | 126.021 |
| | CO | — | 169.949 |
| ASP13 | NH | 8.224 | — |
| | αH | 4.433 | 48.440 |
| | βH | 2.575/2.492 | 35.927 |
| | COO$\underline{H}$$^§$ | 12.45 | — |
| | COO$\underline{H}$$^§$ | 12.70 | — |
| | $\underline{C}$OOH$^§$ | — | 171.300 |
| | $\underline{C}$OOH$^§$ | — | 171.941 |

$^§$: It was not possible to make the allocation of the carboxyl groups to the α- or β-position.

It has furthermore been found that the compound according to the invention has antibacterial activity. Table 2 summarizes the minimum inhibitory concentrations of feglymycin by way of example.

TABLE 2

In vitro activity of feglymycin against gram-positive bacteria in the serial dilution test.
Minimum inhibitory concentration in μg/ml

| Bacterium | (μg/ml) |
|---|---|
| S. aureus SG 511 | 64 |
| S. aureus 285 | 64 |
| S. aureus 503 | 32 |
| S. aureus FH 1982 | 64 |
| S. aureus 701 E | 64 |
| S. aureus 9 Tüb | 64 |
| S. aureus 8236 | 64 |
| S. epidermidis ZH 2C | 64 |
| S. epidermidis 763 | 64 |
| S. epidermidis 799 | 64 |
| S. pyogenes 308A | 32 |
| S. pyogenes 77A | 32 |

Moreover, it has completely surprisingly been found that feglymycin exhibits inhibitory activity on human immunodeficiency viruses. Many active compounds inhibit the virus or viral enzymes only if present in isolated form. Agents of this type are frequently inactive in cell cultures or even in living organisms, such as, for example, man or animals, since they are unable to penetrate the cell wall of the cells in which the viruses are found and replicate. Feglymycin, however, is highly active in the cell culture assay. The IC$_{50}$ is less than 7 μg per ml. The inhibitory activity can be measured by light-microscopic observation of HIV-typical syncytia. In this connection, the reduction in syncytia formation is a measure of the activity of the agent, in this case of feglymycin. It is also possible, however, to determine the activity of feglymycin by measuring the amount of HIV particles in cell culture supernatants, e.g. by means of commercially available p24 antigen tests.

The tolerability of feglymycin in both the active concentration and even in higher concetrations is good. Cytotoxic effects or other toxicities were not observed.

Accordingly, the present invention also relates to the use of the compounds according to the invention as pharmaceuticals, and to the use of the compounds for the production of pharmaceuticals, for the treatment and/or prophylaxis of bacterial and HIV infections.

In addition, the present invention relates to pharmaceutical compositions containing at least one of the compounds according to the invention or its physiologically tolerable salts or chemical equivalents, together with a pharmaceutically effective carrier. These pharmaceutical compositions are useful for the treatment of a bacterial disease or a disease caused by HIV.

The pharmaceuticals according to the invention can be used enterally (orally), parenterally (intramuscularly or intravenously), rectally or locally (topically). They can be administered in the form of solutions, powders (tablets, capsules including microcapsules), ointments (creams or gel), or suppositories. Suitable auxiliaries for formulations of this type are the pharmaceutically customary liquid or solid fillers and extenders, solvents, emulsifiers, lubricants, flavor corrigents, colorants and/or buffer substances. As an expedient dose, 0.1–1000, preferably 0.2–100, mg/kg of body weight are administered. The pharmaceuticals according to the invention are expediently administered in dose units which contain at least the effective daily amount of the compounds according to the invention, e.g. 30–3000, preferably 50–1000, mg.

The following working examples and patent claims are intended to explain the present invention in greater detail.

EXAMPLE 1

Preparation of a spore suspension of the producer strain 100 ml of nutrient solution (20 g of malt extract, 2 g of yeast extract, 10 g of glucose, 0.5 g of $(NH_4)_2HPO_4$ in 1 l of mains water, pH before sterilization: 6.0) in a 500 ml sterile Erlenmeyer flask are inoculated with the strain and incubated on a rotating shaker for 72 hours at 25° C. and 140 rpm. 120 ml of culture fluid are then uniformly distributed in a sterile 500 ml Erlenmeyer flask containing the nutrient medium oatmeal infusion, 2.0 g/l, to which 15 g of agar/l have additionally been added for solidification, and decanted. The cultures are incubated at 25° C. for 10 to 14 days. The resulting spores in the flask are rinsed with 500 ml of deionized water which contains one drop of a commercially available nonionic surfactant (e.g. ®Triton X 100, Serva), immediately reused or stored at −22° C. in 50% glycerol or in 10% dimethyl sulfoxide at −140° C.

EXAMPLE 2

Preparation of a culture or a preculture of the producer strain in an Erlenmeyerflask A sterile 500 ml Erlenmeyer flask containing 100 ml of the nutrient solution described in Example 1 is inoculated with a culture grown on a slant tube or with 0.2 ml of spore suspension and incubated on a shaker in the dark at 140 rpm and 25° C. The maximum production of the compounds of the formula I is achieved after about 72 hours. For inoculating 10 and 100 l fermenters, a 72 hour-old submersed culture (inoculation quantity about 5%) of the same nutrient solution is sufficient.

EXAMPLE 3

Preparation of feglymycin

A 10 l fermenter is operated under the following conditions:

| | | |
|---|---|---|
| Nutrient medium: | 2% oat flakes | |
| | 0.25% trace elements | |
| | Trace elements: | |
| | $CaCl_2$ 2 $H_2O$ | 0.3% |
| | Fe(III) citrate | 0.1% |
| | $MnSO_4$ | 0.02% |
| | $ZnCl_2$ | 0.01% |
| | $CuSO_4$ 5 $H_2O$ | 0.002% |
| | Sodium tetraborate | 0.02% |
| | $CaCl_2$ 6 $H_2O$ | 0.001% |
| | Sodium molybdate | 0.001% |
| Incubation time: | 24 or 48 hours | |
| Incubation temperature: | 28° C. | |
| Stirrer speed: | 200 rpm | |
| Aeration: | 5 I of air/min. | |

The formation of foam can be suppressed by repeated addition of a few drops of ethanolic polyol solution. The production maximum is achieved after 48 hours.

EXAMPLE 4

Isolation of the antibiotic feglymycin 27 l of the culture solution obtained according to Example 3 are centrifuged off and the cell matter (~1.1 L) is extracted by stirring twice with 2.2 l of methanol each time. The combined extracts are concentrated in vacuo and dried, and the dry matter is digested with diethyl ether. The degreased residue washed in this way (40 g) is dissolved in water and applied to a 3 l capacity column packed with the adsorption resin MCI Gel® CHP20P. Column dimensions: width x height: 11.3 cm×30 cm. Elution is carried out with a solvent gradient of 5% isopropanol in water up to 50% isopropanol and the column efflux is collected in fractions of 2 l each.

The feglymycin-containing fractions, which are checked by HPLC analysis, are collected and concentrated in vacuo, and freeze-dried (3.2 g).

EXAMPLE 5

High-pressure liquid chromatography (HPLC) of feglymycin

Column: Nucleosil® 100-5 $C_{18}AB$, 250/4.
Mobile phase: 25% acetonitrile in 0.05% trifluoroacetic acid.
Flow rate: 1 ml per minute
Detection by UV absorption at 210 nm.
The retention time of 12 min. 50 seconds was found for feglymycin.

EXAMPLE 6

Enrichment of feglymycin 3 g of the products obtained according to Example 4 are applied to a column of a capacity of 3 liters packed with Fractogel® TSK HW-40 s (width×height=10 cm×50 cm). The eluent, 50% acetonitrile/10 mM sodium phosphate buffer, pH 7.0, is pumped through the column at a flow rate of 50 ml per minute and the column efflux is collected in fractions (65 ml). The antibiotic feglymycin, 270 mg, is found mainly in fractions 23 to 27.

EXAMPLE 7

Final purification of feglymycin

The enriched antibiotic feglymycin (270 mg), obtained according to Example 6, is separated on a Nucleosil® $12C_{18}AB$ HPLC column (width×height=3.2 cm×25 cm) in a gradient method using 5% to 30% acetonitrile in 0.05% trifluoroacetic acid. The fractions investigated by analytical HPLC (see Example 5) are combined accordingly, concentrated in vacuo and freeze-dried. They yield 21 mg of feglymycin in 97% purity. Molecular weight of feglymycin determined by FAB mass spectrometry: $M+M^+=1900.58$ (monoisotopic peak), 1901.57 (base peak).

EXAMPLE 8

Final purification by preparative HPLC in a phosphate buffer/isopropanol system

The process is carried out as in Example 7, but as an eluent 10 mM potassium phosphate buffer, pH 7, and isopropanol are used. The desalting of the separated components is the same as described in Example 7. The yield is 18 mg of feglymycin in 99% purity.

---

What is claimed is:

1. Feglymycin, a compound of the formula (SEQ ID NO:1)

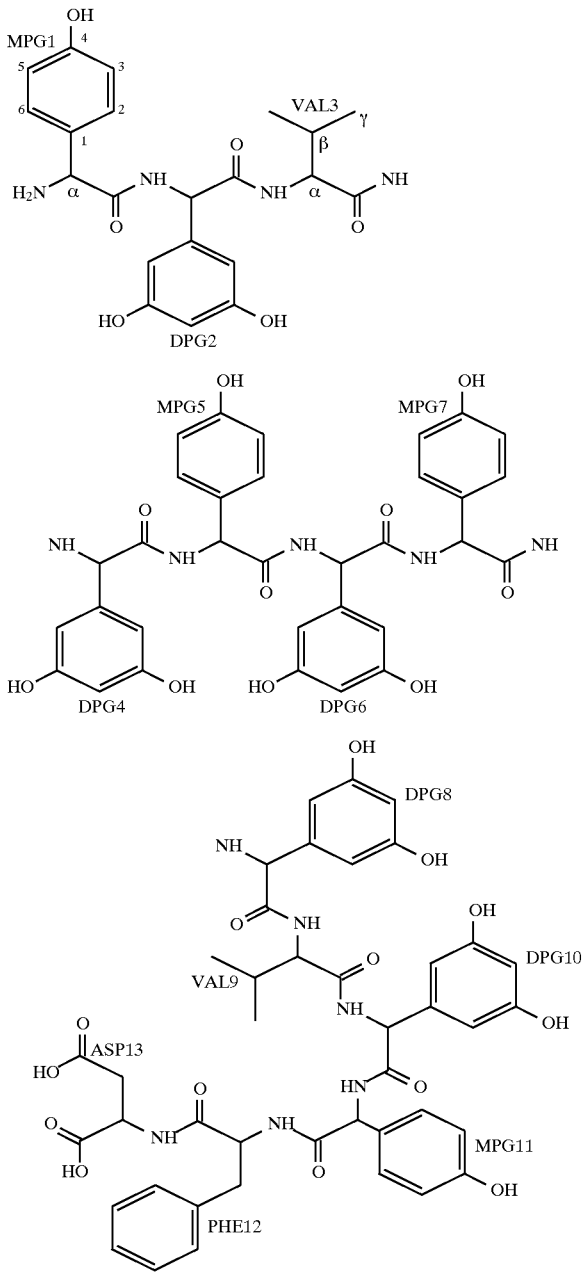

or a physiologically tolerable salt of feglymycin or an obvious chemical equivalent of feglymycin.

2. A compound as claimed in claim 1, which is prepared by fermenting the microorganism DSM 11171 or a variant or mutant thereof and isolating feglymycin.

3. A compound as claimed in claim 2 wherein said feglymycin is converted into a salt of feglymycin or a chemical equivalent of feglymycin.

4. A process for the preparation of the compound as claimed in claim 1, which comprises fermenting the microorganism DSM 11171 or a variant or mutant thereof and isolating feglymycin.

5. A process as claimed in claim 4 wherein said feglymycin is converted into a salt of feglymycin or a chemical equivalent of feglymycin.

6. A process as claimed in claim 4, wherein the fermenting is carried out under aerobic conditions at a temperature between 20° and 35° C. and at a pH between 4 and 10.

7. A method for the treatment of a bacterial disease which comprises administering to a host in need of said treatment a pharmaceutically effective amount of a compound as claimed in claim 2.

8. A method for the treatment of a bacterial disease which comprises administering to a host in need of said treatment a pharmaceutically effective amount of a compound as claimed in claim 1.

9. A pharmaceutical composition comprising at least one compound as claimed in claim 2 or a physiologically tolerable salt of said compound or a chemical equivalent of said compound, together with a pharmaceutically effective carrier.

10. A pharmaceutical composition comprising at least one compound as claimed in claim 1 or a physiologically tolerable salt of said compound or a chemical equivalent of said compound, together with a pharmaceutically effective carrier.

11. A method for the treatment of a bacterial disease which comprises administering to a host in need of said treatment a pharmaceutically effective amount of a pharmaceutical composition as claimed in claim 10.

12. A method for the treatment of a bacterial disease which comprises administering to a host in need of said treatment a pharmaceutically effective amount of a pharmaceutical composition as claimed in claim 9.

13. A process for the production of a pharmaceutical composition comprising at least one compound as claimed in claim 2, which comprises bringing at least one compound as claimed in claim 2 or a physiologically tolerable salt of said compound or a chemical equivalent of said compound into a suitable administration form with a physiologically suitable auxilary, excipient, or combination of auxilary and excipient.

14. A process for the production of a pharmaceutical composition comprising at least one compound as claimed in claim 1 or a physiologically tolerable salt of said compound or a chemical equivalent of said compound, which comprises bringing at least one compound as claimed in claim 1 into a suitable administration form with a physiologically suitable auxilary, excipient, or combination of auxilary and excipient.

15. Streptomyces species DSM 11171.

* * * * *